US 6,528,005 B2

(12) United States Patent
Amagai et al.

(10) Patent No.: US 6,528,005 B2
(45) Date of Patent: Mar. 4, 2003

(54) PROCESS FOR PRODUCING A LENS BY POLYMERIZING BIS(β-EPITHIOPROPYL) ETHER

(75) Inventors: Akikazu Amagai, Tokyo (JP); Motoharu Takeuchi, Tokyo (JP); Atsuki Niimi, Osaka (JP)

(73) Assignee: Mitsubishi Gas Chemical Co., Inc., Tokyo (JP)

( * ) Notice: Subject to any disclaimer, the term of this patent is extended or adjusted under 35 U.S.C. 154(b) by 23 days.

(21) Appl. No.: 09/878,699

(22) Filed: Jun. 11, 2001

(65) Prior Publication Data
US 2001/0041784 A1 Nov. 15, 2001

Related U.S. Application Data

(62) Division of application No. 09/361,051, filed on Jul. 26, 1999, now abandoned.

(30) Foreign Application Priority Data

Aug. 7, 1998 (JP) ............................................ 10-224769

(51) Int. Cl.[7] ........................ B29C 35/02; B29C 39/02; B29C 71/02; C07D 409/12; C08G 75/08
(52) U.S. Cl. .................. 264/331.12; 264/235; 264/299; 264/300; 528/380; 549/90
(58) Field of Search ........................... 528/380; 549/90; 264/331.12, 235, 299, 300

(56) References Cited

U.S. PATENT DOCUMENTS

| 2,962,457 A | 11/1960 | Mackinney | |
| 3,378,522 A | 4/1968 | Martin | |
| 4,748,083 A | 5/1988 | Widmer et al. | 525/523 |
| 5,369,141 A | 11/1994 | Coleman et al. | 523/106 |

FOREIGN PATENT DOCUMENTS

| EP | 0 234 047 A | 9/1987 |
| EP | 0 374 258 A | 6/1990 |
| EP | 0 761 665 A | 3/1997 |
| EP | 0 785 194 A | 7/1997 |
| EP | 0 874 016 A | 10/1998 |
| JP | 3-81320 A | 4/1991 |
| WO | WO 91/19674 A | 12/1991 |

OTHER PUBLICATIONS

Database WPI, Section Ch, Week 199120, Derwent Publications, Ltd., London, GB; AN 1991–144863, XP002122592 of JP 03 081320 (Mitsui Toatsu Chem. Inc.), Apr. 5, 1991 (abstract).
Chemical Abstracts, vol. 114, No. 8, Feb. 25, 1991, Columbus, OH, US; Abstract No. 62894, XP002122591 (abstract), C. Yuanyin et al, Wuhan Daxue Xuebao, Ziran Kexueban, vol. 1, 1990, pp. 83–86.
Database WPI, Section Ch, Week 199925, Derwent Publications, Ltd., London, GB; AN 1999–296553, XP002122593 of JP 11 100435 (Kureha Chem Ind. Co Ltd), Apr. 13, 1999 (abstract).
Patent Abstracts of Japan, vol. 1999, No. 04, Apr. 30, 1999, of JP 11 012273 (Sumitomo Seika Chem Co Ltd) Jan. 19, 1999 (abstract).
Kurnanaliev et al., "New Sulfur–Containing Polymeric Crown Ethers, "IZV Akad. Nauk Resp. Kaz., Ser. Khim. (1992) vol. 6, pp. 43–45.

Primary Examiner—Robert E. L. Sellers
(74) Attorney, Agent, or Firm—Frishauf, Holtz, Goodman & Chick, P.C.

(57) ABSTRACT

A process for producing a lens comprising polymerizing bis(β-epithiopropyl)ether to form a lens.

10 Claims, No Drawings

PROCESS FOR PRODUCING A LENS BY POLYMERIZING BIS(β-EPITHIOPROPYL) ETHER

This is a Division of application Ser. No. 09/361,051, filed Jul. 26, 1999, abandoned.

BACKGROUND OF THE INVENTION

1. Field of the Invention

The present invention relates to an ether compound and a cured resin which is prepared by using the ether compound, exhibits a small chromatic aberration, an excellent tint performance and an excellent antioxidation property and is useful in various applications, particularly as optical materials such as plastic lenses, prisms, optical fibers, substrates of information recording materials and filters, more particularly as a material of plastic lenses of glasses.

2. Description of the Related Arts

Plastic materials have widely been used as various optical materials, particularly as lenses of glasses, because of light weight and toughness. The properties required for optical materials, particularly for lenses of glasses, are a low specific gravity, properties which are occasionally referred to as optical properties i.e., a large refractive index and a large Abbe number, high heat resistance and large strength. A large refractive index is important to decrease the thickness of a lens. A large Abbe number is important to decrease chromatic aberration of a lens. High heat resistance and large strength are important to facilitate fabrication and also from the standpoint of safety. The antioxidation property is also important because optical materials such as plastic lenses must be treated under heating during annealing and coating and are colored by oxidation in these treatments. Tint performance is also required for facilitating production of sunglasses. A typical plastic optical material in early periods of conventional technology is diethylene glycol bisallyl carbonate. This material has a refractive index of about 1.5. Therefore, the thickness of a lens increases and, as a result, the weight cannot be reduced. Materials having a higher refractive index have been desired and various attempts have been made to raise the refractive index to a value of 1.6 or higher. Thermosetting optical materials having a thiourethane structure which are obtained by the reaction of a polythiol compound and a polyisocyanate compound have been proposed (Japanese Patent Publication Heisei 4(1992)-58489 and Japanese Patent Application Laid-Open No. Heisei 5(1993)-148340). Improvement in the refractive index and the Abbe number by the use of these optical materials having the thiourethane structure is insufficient although the improvement can be achieved to some degree. Technology to obtain a lens by polymerization of an epoxy resin or an episulfide resin in combination with a multi-functional compound has been proposed in the specifications of Japanese Patent Application Laid-Open No. Heisei 1(1989)-89615, Japanese Patent Application Laid-Open No. Heisei 3(1991)-81320 and International Patent Application Laid-Open No. wo8910575. However, the optical materials of the conventional technology which are obtained by curing an epoxy compound or an episulfide compound by polymerization have insufficient refractive indices, poor Abbe numbers and insufficient balances between the refractive index and the Abbe number. The thickness and the weight can be decreased by the conventional compounds containing sulfur to some degree. However, it is natural that an optical material having a still larger refractive index is desired. A material simultaneously exhibiting a large refractive index and a large Abbe number is also desired. Generally, the larger the refractive index, the smaller the Abbe number. Plastic materials obtained from conventional compounds such as diethylene glycol bisallyl carbonate, combinations of a polythiol compound and a polyisocyanate compound, epoxy compounds and episulfide compounds have the maximum Abbe number of about 50 to 55 when the refractive index is 1.50 to 1.55, about 40 when the refractive index is 1.60 and about 30 when the refractive index is 1.65. It is impossible to achieve an excellent balance between the refractive index and the Abbe number such as an Abbe number of about 40 or larger with a refractive index of 1.60 or an Abbe number of about 35 or larger with a refractive index of 1.65. The present inventors have disclosed optical materials comprising sulfur and carbon atoms as the main components and exhibiting an excellent balance between the refractive index and the Abbe number (for example, Japanese Patent Application Laid-Open No. Heisei 9(1997)-110979). However, some of these materials exhibit insufficient tint performance and antioxidation property.

SUMMARY OF THE INVENTION

An object of the present invention is to develop an optical material which has a decreased thickness and simultaneously exhibits a small chromatic aberration, an excellent tint performance and an excellent antioxidation property. Conventional optical materials which are, typically, materials obtained from a polythiol compound and an isocyanate compound or an episulfide compound have drawbacks in that improvement in the refractive index is limited, that an increase in the refractive index causes a decrease in the Abbe number, that a simultaneous improvement in the refractive index and the Abbe number by a structure containing sulfur in a large amount causes deterioration in the tint performance and the antioxidation property and that, as the result, it is difficult to simultaneously achieve an excellent balance between a sufficiently large refractive index and a sufficiently large Abbe number, an excellent tint performance and an excellent antioxidation property.

It was found that the above drawbacks can be overcome by:

(1) An ether compound having a structure represented by following formula (1) and at least one of a structure represented by following formula (2) and a structure represented by following formula (3):

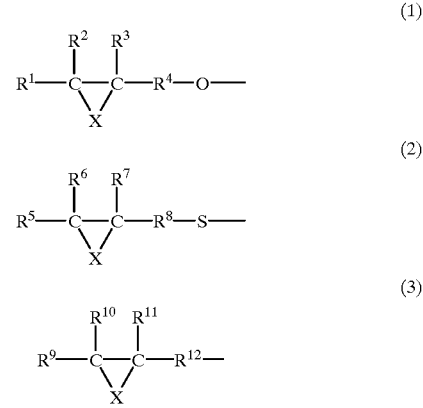

wherein X represents S or O, the average number of S represented by X is 50% or more of a total number of S and O constituting the three-membered rings, $R^4$, $R^8$ and $R^{12}$ each represents a hydrocarbon group having 1 to 10 carbon atoms and $R^1$ to $R^3$, $R^5$ to $R^7$ and $R^9$ to $R^{11}$ each represents hydrogen atom or a hydrocarbon group having 1 to 10 carbon atoms;

(2) A bis(β-epithioalkyl) ether compound represented by following formula (4):

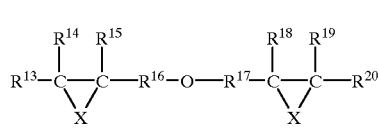

(4)

wherein $R^{16}$ and $R^{17}$ each represents a hydrocarbon group having 1 to 10 carbon atoms, $R^{13}$ to $R^{15}$ and $R^{18}$ to $R^{20}$ each represents hydrogen atom or a hydrocarbon group having 1 to 10 carbon atoms and X represents S or O;

(3) A cured resin obtained by polymerizing a compound described in any of (1) and (2);

(4) A process for producing a cured resin comprising polymerizing a compound described in any of (1) and (2); and (5) A lens comprising a cured resin described in (3).

In other words, it is found that the drawbacks of the conventional optical materials can be overcome when the cured resin of the present invention is used as the optical material.

DESCRIPTION OF THE PREFERRED EMBODIMENTS

The diepisulfide compound which is used as the ether compounds in the present invention can be produced by converting epoxy groups in a compound represented by following formula (5) such as a glycidyl ether into the thia group by the reaction with an agent to form a thia group.

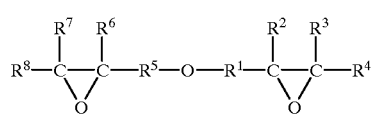

(5)

In formula (5), $R^1$ and $R^5$ each represents a hydrocarbon group having 1 to 10 carbon atoms and $R^2$ to $R^4$ and $R^6$ to $R^8$ each represents hydrogen atom or a hydrocarbon group having 1 to 10 carbon atoms.

Examples of the agent to form a thia group include salts of thiocyanic acid, thiourea, triphenylphosphine sulfide and 3-methylbenzothiazole-2-thione. The salts of thiocyanic acid and thiourea are preferable.

When a salt of thiocyanic acid is used as the agent to form a thia group in the production of the ether compound of the present invention from the compound represented by formula (5), it is preferable that the salt of thiocyanic acid is an alkali metal salt or an alkaline earth metal salt of thiocyanic acid. Potassium thiocyanate and sodium thiocyanate are more preferable. Stoichiometrically, the salt of thiocyanate or thiourea is used in an amount by mol corresponding to the amount of the epoxy group in the epoxy compound represented by formula (5). However, an amount exceeding or less than the stoichiometrical amount may be used when the purity of the product, the reaction rate and economy are taken into account. It is preferable that an amount in the range of 1 to 5 times the stoichiometrical amount is used for the reaction. It is more preferable that an amount in the range of 1 to 2.5 times the stoichiometrical amount is used. The reaction may be conducted without any solvent or in a solvent. When a solvent is used, it is preferable that any one of the salt of thiocyanic acid, thiourea and the glycidyl ether represented by formula (5) is soluble in the solvent. Examples of the solvent include water; alcohols such as methanol, ethanol and isopropanol; ethers such as diethyl ether, tetrahydrofuran and dioxane; hydroxyethers such as methylcellosolve, ethylcellosolve and butylcellosolve; aromatic hydrocarbons such as benzene, toluene and xylene; and halogenated hydrocarbons such as dichloroethane, chloroform and chlorobenzene. It is effective that a combination of these solvents such as a combination of an ether, a hydroxyether, a halogenated hydrocarbon or an aromatic hydrocarbon with an alcohol is used. To obtain a desirable result of the reaction, it is also effective that an acid or an acid anhydride is added to the reaction liquid as the polymerization inhibitor. Examples of the acid and the acid anhydride include nitric acid, hydrochloric acid, sulfuric acid, fuming sulfuric acid, boric acid, arsenic acid, phosphoric acid, cyanic acid, acetic acid, peracetic acid, thioacetic acid, oxalic acid, tartaric acid, propionic acid, butyric acid, succinic acid, maleic acid, benzoic acid, nitric anhydride, sulfuric anhydride, boron oxide, arsenic pentaoxide, phosphorus pentaoxide, chromic anhydride, acetic anhydride, propionic anhydride, butyric anhydride, succinic anhydride, maleic anhydride, benzoic anhydride, phthalic anhydride, silica gel, silica-alumina and aluminum chloride. Combinations of these acids and acid anhydrides can also be used. The acid and the acid anhydride is generally used in an amount of 0.001 to 10% by weight and preferably 0.01 to 1% by weight of the total amount of the reaction liquid. The reaction is generally conducted at a temperature in the range of 0 to 100° C. and preferably in the range of 20 to 70° C. The time of the reaction is not particularly limited as long as the reaction is completed in the above conditions. It is generally suitable that the reaction is conducted for 20 hours or less. Stability of the obtained compound can be improved by washing the reaction product with an acidic aqueous solution. Examples of an acid used for the acidic aqueous solution include nitric acid, hydrochloric acid, sulfuric acid, boric acid, arsenic acid, phosphoric acid, cyanic acid, acetic acid, peracetic acid, thioacetic acid, oxalic acid, tartaric acid, succinic acid and maleic acid. A single type or a mixture of two or more types of these acids may be used. The aqueous solution of the acid is generally effective when pH is in the range of 6 or less and more effective when pH is in the range of 3 or less.

As an alternative process for producing the ether compound, the epoxy compound represented by formula (5) is produced, for example, from a corresponding unsaturated alkyl ether compound by oxidation of the unsaturated bonds with an organic peracid, an alkyl hydroperoxide or hydrogen peroxide and then the desired ether compound is formed from the obtained epoxy compound represented by formula (5) in accordance with the above process.

As still another process, it is advantageous that the ether compound is produced by the reaction of removing a hydrogen halide from a halomercaptan compound represented by the following formula (6):

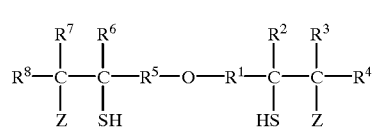

(6)

wherein $R^1$ and $R^5$ each represents a hydrocarbon group having 1 to 10 carbon atoms, $R^2$ to $R^4$ and $R^6$ to $R^8$ each represents hydrogen atom or a hydrocarbon group having 1 to 10 carbon atoms and Z represents chlorine atom or bromine atom.

Preferable examples of the ether compound of the present invention include the following diepisulfide ether compounds:

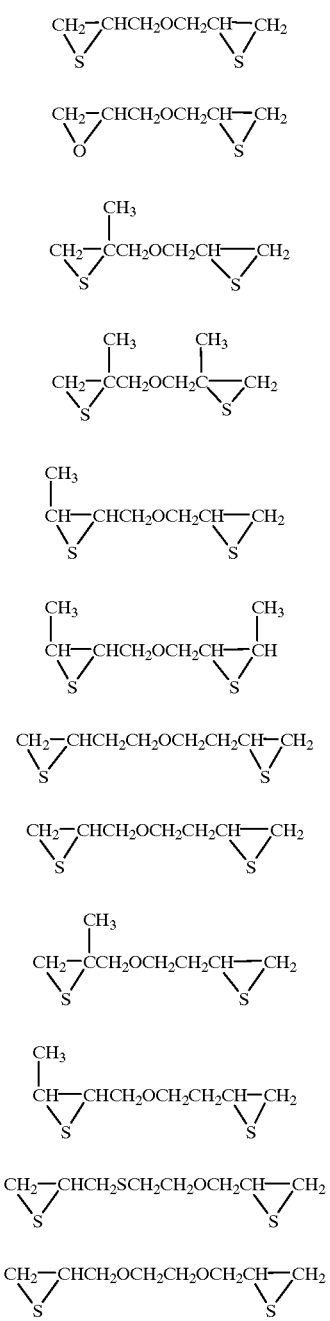

Among these compounds, the ether compounds represented by formulae (7) to (12) are preferable. The ether compounds represented by formulae (7), (9) and (10) are more preferable.

The novel optical material of a cure resin of the present invention can be produced by polymerization of the above diepisulfide ether compound by heating in the presence or the absence of a curing catalyst. It is preferable that the polymerization is conducted in the presence of a curing catalyst. As the curing catalyst, amines, phosphines, mineral acids, Lewis acids, organic acids, silicic acids and tetrafluo- roboric acid are used. Specific examples of the curing catalyst are as follows:

(1) Primary monoamines such as ethylamine, n-propylamine, sec-propylamine, n-butylamine, sec-butylamine, isobutylamine, tert-butylamine, pentylamine, hexylamine, heptylamine, octylamine, decylamine, laurylamine, myristylamine, 1,2-dimethylhexylamine, 3-pentylamine, 2-ethylhexylamine, allylamine, aminoethanol, 1-aminopropanol, 2-aminopropanol, aminobutanol, aminopentanol, aminohexanol, 3-ethoxypropylamine, 3-propoxypropylamine, 3-isopropoxypropylamine, 3-butoxypropylamine, 3-isobutoxypropylamine, 3-(2-ethylhexyloxy)propylamine, aminocyclopentane, aminocyclohexane, aminonorbornene, aminomethylcylcohexane, aminobenzene, benzylamine, phenetylamine, α-phenylethylamine, naphthylamine and furfurylamine; primary polyamines such as ethylenediamine, 1,2-diaminopropane, 1,3-diaminopropane, 1,2-diaminobutane, 1,3-diaminobutane, 1,4-diaminobutane, 1,5-diaminopentane, 1,6-diaminohexane, 1,7-diaminoheptane, 1,8-diaminooctane, dimethylaminopropylamine, diethylaminopropylamine, bis-(3-aminopropyl) ether, 1,2-bis-(3-aminopropoxy)ethane, 1,3-bis-(3-aminopropoxy)-2,2'-dimethylpropane, aminoethylethanolamine, 1,2-, 1,3- and 1,4-bisaminocyclohexanes, 1,3-and 1,4-bisaminomethylcyclohexanes, 1,3- and 1,4-bisaminoethylcyclohexanes, 1,3- and 1,4-bisaminopropylcyclohexanes, hydrogenated 4,4'-diaminodiphenylmethane, 2- and 4-aminopiperidines, 2- and 4-aminomethylpiperidines, 2- and 4-aiminoethylpiperidines, N-aminoethylpiperidine, N-aminopropylpiperidine, N-aminoetliylmorpholine, N-aminopropylmorpholine, isophoronediamine, menthanediamine, 1,4-bisaminopropylpiperadine, o-, m- and p-phenylenediamines, 2,4- and 2,6-tolylenediamines, 2,4-toluenediamine, m-aminobenzylamine, 4-chloro-o-phenylenediamine, tetrachloro-p-xylylenediamine, 4-methoxy-6-methyl-m-phenylenediamine, m- and p-xylylenediamines, 1,5- and 2,6-naphthalenediamines, benzidine, 4,4'-bis(o-toluidine), dianisidine, 4,4'-diaminodiphenylmethane, 2,2-(4,4'-diaminodiphenyl)propane, 4,4'-diaminodiphenyl ether, 4,4'-thiodianiline, 4,4'-diaminodiphenyl sulfone, 4,4'-diaminoditolyl sulfone, methylenebis(o-chloroaniline), 3,9-bis(3-aminopropyl)-2,4,8,10-tetraoxaspiro [5,5]undecane, diethylenetriamine, iminobispropylamine, methyliminobispropylamine, bis(hexamethylene)triamine, triethylenetetrainime, tetraethylenepentamine, pentaethylenehaxamine, N-aminoethylpiperadine, N-aminopropylpiperadine, 1,4-bis(aminoethylpiperadine), 1,4-bis(aminopropylpiperadine), 2,6-diaminopyridine and bis(3,4-diaminophenyl) sulfone; secondary monoamines such as diethylamine, dipropylamine, di-n-butylamine, di-sec-butylamine, diisobutylaimine, di-n-pentylamine, di-3-pentylamine, dihexylamine, dioctylamine, di(2-ethylhexyl)amine, methylhexylamine, diallylamine, pyrrolidine, piperidine, 2-, 3- and 4-picolines, 2,4-, 2,6- and 3,5-lupetidines, diphenylamine, N-methylaniline, N-ethylaniline, dibenzylamine, methylbenzylamine, dinaphthylamine, pyrrol, indoline, indole and morpholine; secondary polyamines such as N,N'-dimethylethylenediamine, N,N'-dimethyl-1,2-diaminopropane, N,N'-dimethyl-1,3-diaminopropane, N,N'-dimethyl-1,2-diaminobutane, N,N'-dimethyl-1,3-diaminobutane, N,N'-dimethyl-1,4-diaminobutane, N,N'-dimethyl-1,5-diaminopentane, N,N'-dimethyl-1,6-diaminohexane, N,N'-dimethyl-1,7-diaminoheptane, N,N'- diethylethylenediamine, N,N'-diethyl-1,2-diaminopropane, N,N'-diethyl-1,3-diaminopropane, N,N'-diethyl-1,2-diaminobutane, N,N'-diethyl-1,3-diaminobutane, N,N'-diethyl-1,4-diaminobutane, N,N'-diethyl-1,6-diaminohexane, piperadine, 2-methylpiperadine, 2,5- and 2,6-dimethylpiperadines, homopiperadine, 1,1-di-(4-piperidyl)methane, 1,2-di-(4-piperidyl)ethane, 1,3-di-(4-piperidyl)propane, 1,4-di(4-piperidyl)butane and tetramethylguanidine; tertiary amines such as trimethylamine, triethylamine, tri-n-propylamine, triisopropylamine, tri-1,2-dimethylpropylamine, tri-3-methoxypropylamine, tri-n-butylamine, triisobutylamine, tri-sec-butylamine, tri-n-pentylamine, tri-3-pentylamine, tri-n-hexylamine, tri-n-octylamine, tri-2-ethylhexylamine, tridodecylamine, trilaurylamine, tricyclohexylamine, dicyclohexylethylamine, monocyclohexyldiethylamine, N,N-dimethylhexylamine, N-methyldihexylamine, N,N-dimethylcyclohexylamine, N-methyldicyclohexylamine, triethanolamine, N,N-diethylethanolamine, N-ethyldiethanolamine, tribenzylamine, N,N-dimethylbenzylamine, diethylbenzylamine, triphenylamine, N,N-dimethylamino-p-cresol, N,N-dimethylaminomethylphenol, 2-(N,N-dimethylaminomethyl)phenol, N,N-dimethylaniline, N,N-diethylaniline, pyridine, quinoline, N-methylmorpholine, N-methylpiperidine and 2-(2-dimethylaminoethoxy)-4-methyl-1,3,2-dioxabornane; tertiary polyamines such as tetramethylethylenediamine, pyrazine, N,N'-dimethylpiperadine, N,N'-bis((2-hydroxy)-propyl)piperadine, hexamethylenetetramine, N,N,N',N'-tetramethyl-1,3-butaneamine, 2-dimethylamino-2-hydroxypropane, diethyaminoethanol, N,N,N-tris(3-dimethylaminopropyl)amine, 2,4,6-tris(N,N-dimethylaminomethyl)phenol and heptamethylisobiguanide; imidazoles such as imidazole, N-methylimidazole, 2-methylimidazole, 4-methylimidazole, N-ethylimidazole, 2-ethylimidazole, 4-ethylimidazole, N-butylimidazole, 2-1-butylimidazole, N-undecylimidazole, 2-undecylimidazole, N-phenylimidazole, 2-phenylimidazole, N-benzylimidazole, 2-benzylimidazole, 1-benzyl-2-methylimidazole, N-(2'-cyanoethyl)-2-methylimidazole, N-(2'-cycanoethyl)-2-undecylimidazole, N-(2'-cyanoethyl)-2-phenylimidazole, 3,3-bis-(2-ethyl-4-methylimidazolyl)methane, addition products of alkylimidazoles and isocyanuric acid and condensation products of alkylimidazoles and formaldehyde; and amidines such as 1,8-diazabicyclo-(5,4,0)undecene-7,1,5-diazabicyclo(4,3,0)nonene-5,6-dibutylamino-1,8-diazabicyclo(5,4,0)undecene-7.

(2) Quaternary ammonium salts of the amines described above in (1) with halogens, mineral acids, Lewis acids, organic acids, silicic acid and tetrafluoroboric acid.

(3) Complexes of the amines described above in (1) with borane and trifluoroboron.

(4) Phosphines such as trimethylphosphine, triethylphosphine, triisopropylphosphine, tri-n-butylphosphine, tricyclohexylphosphine, triphenylphosphine, tribenzylphosphine, dimethylphenylphosphine, diethylphenylphosphine, ethyldiphenylphosphine, and chlorodiphenylphosphine. Mineral acids such as hydrochloric acid, sulfuric acid, nitric acid, phosphoric acid and carbonic acid. Half-esters of these mineral acids. Lewis acids such as boron trifluoride and boron trifluoride etherates. Organic acids such as carboxylic acids and half-esters of organic acids. Silicic acids and tetrafluoroboric acid.

Among these compounds, primary monoamines, secondary monoamines, tertiary monoamines, tertiary polyamines, imidazoles, amidines, quaternary ammonium salts and phosphines are preferable because these compounds cause little coloring of the cured products. Compounds having one or less group which can react with the episulfide group such as secondary monoamines, tertiary monoamines, tertiary polyamines, imidazoles, amidines, quaternary ammonium salts and phosphines are more preferable. A single type or a mixture of two or more types of these compounds may be used. The above curing catalyst is used in an amount generally in the range of 0.0001 to 1.0 mol, preferably in the range of 0.0001 to 0.5 mol, more preferably in the range of 0.0001 mol or more and less than 0.1 mol and most preferably in the range of 0.0001 to 0.05 mol per 1 mol of the diepisulfide ether compound. When the amount of the curing catalyst exceeds the above range, the refractivity index and heat resistance of the cured product are inferior and the cured product is colored. When the amount is less than the above range, the curing does not proceed sufficiently and heat resistance becomes insufficient.

It is also possible that compounds having one or more SH groups is used in the optical material obtained by curing the ether compound of the present invention by polymerization as the antioxidant component singly or in combination with conventional antioxidants to provide the material with a further improved oxidation resistance. Examples of the compound having one or more SH groups include mercaptans, thiophenols and mercaptans and thiophenols having unsaturated groups such as vinyl group, aromatic vinyl groups, methacryl group, acryl group and ally group. Specific examples of the mercaptan include monomercaptans such as methyl mercaptan, ethyl mercaptan, n-propyl mercaptan, n-butyl mercaptan, allyl mercaptan, n-hexyl mercaptan, n-octyl mercaptan, n-decyl mercaptan, n-dodecyl mercaptan, n-tetradecyl mercaptan, n-hexadecyl mercaptan, n-octadecyl mercaptan, cyclohexyl mercaptan, isopropyl mercaptan, tert-butyl mercaptan, tert-nonyl mercaptan, tert-dodecyl mercaptan, benzyl mercaptan, 4-chlorobenzyl mercaptan, methyl thioglycolate, ethyl thioglycolate, n-butyl thioglycolate, n-octyl thioglycolate, methyl (3-mercaptopropionate), ethyl (3-mercaptopropionate), 3-methoxybutyl (3-mercaptopropionate), n-butyl (3-mercaptopropionate), 2-ethylhexyl (3-mercaptopropionate) and n-octyl (3-mercaptopropionate); and polymercaptans such as methanedithiol, 1,2-dimercaptoethane, 1,2-dimercaptopropane, 2,2-dimercaptopropane, 1,3-dimercaptopropaine, 1,2,3-trimercaptopropane, 1,4-dimercaptobutane, 1,6-dimercaptohexane, bis(2-mercaptoethyl) sulfide, 1,2-bis(2-mercaptoethylthio)ethane, 1,5-dimercapto-3-oxapentane, 1,8-dimercapto-3,6-dioxaoctane, 2,2-dimethylpropane-1,3-dithiol, 3,4-dimethoxybutane-1,2-dithiol, 2-mercaptomethyl-1,3-dimercaptopropane, 2-mercaptomethyl-1,4-dimercaptobutane, 2-(2-mercaptoethylthio)-1,3-dimercaptopropane, 1,2-bis(2-mercaptoethylthio)-3-mercaptopropane, 1,1,1-tris(mercaptomethyl)propane, tetrakis-(mercaptomethyl)methane, ethylene glycol bis(2-mercaptoacetate), ethylene glycol bis(3-mercaptopropionate), 1,4-butanediol bis(2-mercaptoacetate), 1,4-butanediol bis(3-mercaptopropionate), trimethylolpropane tris(2-mercaptoacetate), trimethylolpropane tris(3-mercaptopropionate), pentaerythritol tetrakis(2-mercaptoacetate), pentaerythritol tetrakis(3-mercaptopropionate), 1,1-dimercaptocyclohexane, 1,4-dimercaptocyclohexane, 1,3-dimercaptocyclohexane, 1,2-dimercaptocyclohexane, 1,4-bis(mercaptomethyl)- cyclohexane, 1,3-bis-(mercaptomethyl)cyclohexane, 2,5-bis (mercaptomethyl)-1,4-dithiane, 2,5-bis(2-mercaptoethy)-1, 4-dithiane, 2,5-bis(mercaptomethyl)-1-thiane, 2,5-bis(2-mercaptoethyl)-1-thiane, 1,4-bis(mercaptomethyl)benzene, 1,3-bis(mercaptomethyl)benzene, bis(4-mercaptophenyl) sulfide, bis(4-mercaptophenyl) ether, 2,2-bis(4-mercaptophenyl)propane, bis(4-mercaptomethylphenyl) sulfide, bis(4-mercaptomethylphenyl) ether, 2,2-bis(4-mercaptomethylphenyl)propane, 2,5-dimercapto-1,3,4-thiadiazole and 3,4-thiophenedithiol.

Specific examples of the thiophenol include thiophenol, 4-tert-butylthiophenol, 2-methylthiophenol, 3-methylthiophenol, 4-methylthiophenol, 1,2-dimercaptobenzene, 1,3-dimercaptobenzene and 1,4-dimercaptobenzene.

Specific examples of the mercaptans and thiophenols having unsaturated groups are as follows.

Specific examples of the mercaptan having unsaturated groups include allyl mercaptan, 2-vinylbenzyl mercaptan, 3-vinylbenzyl mercaptan and 4-vinylbenzyl mercaptan.

Specific examples of the thiophenol having unsaturated groups include 2-vinylthiophenol, 3-vinylthiophenol and 4-vinylthiophenol.

To improve the tint performance of the optical material obtained by curing the ether compound of the present invention by polymerization, the material may further contain a compound having one or more active hydrogen atoms in one molecule, at least one of which is an active hydrogen atom other than that of the SH group.

The active hydrogen atom in the present invention means a reactive hydrogen atom other than the hydrogen atom of the SH group such as hydrogen atoms in hydroxyl group, carboxyl group and amide group and hydrogen atoms at the 2-position of 1,3-diketones, 1,3-dicarboxylic acids, esters of 1,3-dicarboxylic acids, 3-ketocarboxylic acids, and esters of 3-ketocarboxylic acids. Examples of the compound having at least one active hydrogen atom in one molecule include alcohols, phenols, mercaptoalcohols, hydroxythiophenols, carboxylic acids, mercaptocarboxylic acids, hydroxycarboxylic acids, amides, 1,3-diketones, 1,3-dicarboxylic acids, esters of 1,3-dicarboxylic acids, 3-ketocarboxylic acids, esters of 3-ketocarboxylic acids, and compounds having unsaturated groups such as alcohols, phenols, mercaptoalcohols, hydroxythiophenols, carboxylic acids, mercaptocarboxylic acids, hydroxycarboxylic acids, amides, 1,3-diketones, 1,3-dicarboxylic acids, esters of 1,3-dicarboxylic acids, 3-ketocarboxylic acids and esters of 3-ketocarboxylic acids having vinyl group, aromatic vinyl groups, methacrylic group, acrylic group and allyl group. Examples of the alcohol include monohydric alcohols such as methanol, ethanol, n-propyl alcohol, isopropyl alcohol, n-butyl alcohol, isobutyl alcohol, sec-butyl alcohol, tert-butyl alcohol, n-pentyl alcohol, isopentyl alcohol, n-hexyl alcohol, n-heptyl alcohol, n-octyl alcohol, n-nonyl alcohol, n-decyl alcohol, n-dodecyl alcohol, cyclopentanol, cyclohexanol, 2-methylthioethanol, 2-ethylthioethanol, 2-(n-dodecylthio)ethanol and n-dodecyl hydroxyethyl sulfoxide; and polyhydric alcohols such as ethylene glycol, propylene glycol, 1,3-propanediol, diethylene glycol, triethylene glycol, polyethylene glycol, 1,3-butylene glycol, 1,6-hexanediol, neopentyl glycol, polypropylene glycol, glycerol, pentaerythritol monomethacrylate, pentaerythritol monoacrylate, pentaerythritol dimethacrylate, pentaerythritol diacrylate, 2,5-dimethyl-3-hexane-2,5-diol, 2,5-dimethylhexane-2,5-diol, trimethylolpropane, pentaerythritol, hydrogenated bisphenol A, 2-hydroxyethyl isocyanurate and 2-hydroxyethyl cyanurate.

Examples of the phenol include phenol, o-cresol, m-cresol, p-cresol, catechol, resorcinol, hydroquinone, o-hydroxybenzaldehyde, m-hydroxybenzaldehyde, p-hydroxybenzaldehyde, bisphenol A, bisphenol F and bisphenol Z.

Examples of the mercaptoalcohol include 2-mercaptoethanol, 3-mercaptopropanol, 2-mercaptopropanol, 2-hydroxypropylmercaptan, 2-phenyl-2-mercaptoethanol, 2-phenyl-2-hydroxyethylmercaptan, 3-mercapto-1,2-propanediol, 2-mercapto-1,3-propanediol, 2,3-dimercaptopropanol, 1,3-dimercapto-2-propanol, 2,2-dimethylpropane-1,3-dithiol and glyceryl dithioglycolate.

Examples of the hydroxythiophenol include 2-hydroxythiophenol, 3-hydroxythiophenol and 4-hydroxythiophenol.

Examples of the carboxylic acid include formic acid, acetic acid, propionic acid, butyric acid, valeric acid, caproic acid, caprylic acid, methyl mercaptopropionate, oxalic acid, malonic acid, succinic acid, glutaric acid, adipic acid, cyclohexanecarboxylic acid, benzoic acid, o-toluic acid, m-toluic acid, p-toluic acid, 2-methoxybenzoic acid, 3-methoxybenzoic acid, phthalic acid, isophthalic acid, terephthalic acid, thiodipropionic acid and dithiodipropionic acid.

Examples of the mercaptocarboxylic acid include thioglycolic acid, 2-thiopropionic acid, 3-thiopropionic acid, thiolactic acid, mercaptosuccinic acid, thiomalic acid, N-(2-mercaptopropionyl)glycine, 2-mercaptobenzoic acid, 2-mercaptonicotinic acid, 3,3-dithioisobutyric acid, dithioglycolic acid, and dithiopropionic acid. Examples of the hydroxycarboxylic acid include hydroxyacetic acid, α-hydroxypropionic acid, β-hydroxypropionic acid, α-hydroxybutyric acid, β-hydroxybutyric acid, γ-hydroxybutyric acid, salicylic acid, 3-hydroxybenzoic acid and 4-hydroxybenzoic acid.

Examples of the amide include formamide, N-methylformamide, acetamide, N-methylacetamide, phthalamide, isophthalamide, terephthalamide, benzamide, toluamide, 4-hydroxybenzamide and 3-hydroxybenzamide.

Examples of the 1,3-diketone include acetylacetone and cyclohexane-1,3,5-trione.

Examples of the 1,3-dicarboxylic acid and the ester thereof include malonic acid, 2-methylmalonic acid and mono- and diesters thereof.

Examples of the 3-ketocarboxylic acid and the ester thereof include acetoacetic acid and esters thereof.

Specific examples of the alcohol, phenol, mercaptan, thiophenol, mercaptoalcohol, carboxylic acid and amide having unsaturated groups are as follows.

Examples of the alcohol having an unsaturated group include monohydroxy compounds such as 2-hydroxyethyl methacrylate, 2-hydroxyethyl acrylate, 3-hydroxypropyl methacrylate, 3-hydroxypropyl acrylate, 2-hydroxypropyl methacrylate, 2-hydroxypropyl acrylate, 1,3-dimethacryloxy-2-propanol, 1,3-diacryloxy-2-propanol, 1-acryloxy-3-methacryloxy-2-propanol, penitaerythritol trimethacrylate, pentaerythritol triacrylate, bis(2,2,2-trimethylolethyl) ether pentamethacrylate, bis(2,2,2-trimethylolethyl) ether pentaacrylate, trimethylolpropane dimethacrylate, trimethylolprop-ane diacrylate, allyl alcohol, crotyl alcohol, methyl vinyl carbinol, cinnamyl alcohol, 4-vinylbenzyl alcohol, 3-vinylbenzyl alcohol, 2-(4-vinylbenzylthio)ethanol. 2-(3-vinylbenzylthio)ethanol, 1,3-bis(4-vinylbenzylthio)-2-propanol, 1,3-bis(3-vinylbenzylthio)-2-propanol, 2,3-bis(4-vinylbenzylthio)-1-propanol, 2,3-bis(3-vinylbenzylthio)-1-propanol, 3-phenoxy-2-hydroxylpropyl acrylate, 2-hydroxyethyl isocyanurate bis(acrylate), 2-hydroxyethyl isocyanurate bis(methacrylate), 2-hydroxyethyl cyanurate bis(acrylate), 2-hydroxyethyl cyanurate bis(methacrylate), 3-methyl-1-butyn-3-ol, 3-methyl-1-pentyn-3-ol and propargyl alcohol; polyhydroxy compounds such as pentaerythritol dimethacrylate, pentaerythritol diacrylate, pentaerythritol monomethacrylate, pentaerythritol monoacrylate, trimethylolpropane monomethacrylate, trimethylolpropane monoacrylate, 2-hydroxyethyl isocyanurate mono(acrylate), 2-hydroxyethyl isocyanurate mono-(methacrylate), 2-hydroxyethyl cyanurate mono(acrylate) and 2-hydroxyethyl cyanurate mono(methacrylate); and unsaturated polyhydroxy compounds formed by the addition reaction of acrylic acid or methacrylic acid with epoxy compounds which are described later such as 2,2-bis[4-(2-hydroxy-3-methacryloxypropoxy)phenyl]propane.

Examples of the phenol having an unsaturated group include 2-vinylphenol, 3-vinylphenol and 4-vinylphenol.

Examples of the mercaptoalcohol having an unsaturated group include 2-(4-vinylbenzylthio)-2-mercaptoethanol and 2-(3-vinylbenzylthio)-2-mercaptoethanol.

Examples of the carboxylic acid having an unsaturated group include acrylic acid, methacrylic acid, crotonic acid, monohydroxyethyl acrylate phthalate, maleic acid, fumaric acid, monoallyl phthalate and cinnamic acid.

Examples of the amide having an unsaturated group include amides of α,β-unsaturated carboxylic acids such as acrylic acid, methacrylic acid, maleic acid, maleic anhydride and fumaric acid; and N-vinylformamide.

From the standpoint of heat resistance, preferable examples of the above compounds include mercaptoalcohols, hydroxythiophenols and alcohols having unsaturated groups.

A single type or a mixture of two or more types of the above compound may be used.

The ether compound of the present invention may be cured by polymerization in combination with a compound having one or more functional groups which are reactive with the episulfide group and/or the epoxy group, a compound having one or more functional groups which are reactive with the episulfide group and/or the epoxy group and one or more other homopolymerizable functional groups or a compound having one or more homopolymerizable functional group.

Examples of the compound having one or more functional groups which are reactive with the episulfide group and/or the epoxy group include epoxy compounds, conventional episulfide compounds and polybasic carboxylic acid anhydrides.

Examples of the compound having one or more functional groups which are reactive with the episulfide group and/or the epoxy group and one or more other homopolymerizable functional groups include epoxy compounds, episulfide compounds and carboxylic acid anhydrides having unsaturated groups such is methacryl group, acryl group, allyl group, vinyl group and aromatic vinyl groups.

Examples of the compound having one or more homopolymerizable functional group include compounds having unsaturated groups such as methacryl group, acryl group, allyl group, vinyl group and aromatic vinyl groups.

Further examples of the above compound include compounds having one epoxy group or episulfide group. Specific examples of such compounds include monoepoxy compounds such as ethylene oxide, propylene oxide and glycidol; glycidyl esters of monocarboxylic acids such as acetic acid, propionic acid and benzoic acid; glycidyl ethers such as methyl glycidyl ether, ethyl glycidyl ether, propyl glycidyl ether and butyl glycidyl ether; monoepisulfide compounds such as ethylene sulfide and propylene sulfide; thioglycidyl esters having structures derived from the above monocarboxylic acids and thioglycidol (1,2-epithio-3-hydroxypropane); and thioglycidyl ethers such as methyl thioglycidyl ether (1,2-epithiopropyloxymethane), ethyl thioglycidyl ether, propyl thioglycidyl ether and butyl thioglycidyl ether. Among these compounds, compounds having one episulfide group are preferable.

Examples of the polybasic carboxylic acid anhydride include anhydrides of polybasic carboxylic acid compounds described below which are used for producing epoxy compounds of glycidyl ethers described below by condensation with epihalohydrins.

Examples of the compound having two or more functional groups which are reactive with the episulfide group are as follows: epoxy compounds derived from phenols which are produced by condensation of epihalohydrins with polvhydric phenols such as hydroquinone, catechol, resorcinol, bisphenol A, bisphenol F, bisphenol sulfone, bisphenol ether, bisphenol sulfide, halogenated bisphenol A and novolak resins; epoxy compounds derived from alcohols which are produced by condensation of epihalohydrins with polyhydric alcohols such as ethylene glycol, diethylene glycol, triethylene glycol, polyethylene glycol, propylene glycol, dipropylene glycol, polypropylene glycol, 1,3-propanediol, 1,4-butanediol, 1,6-hexanediol, neopentyl glycol, glycerol, trimethylolpropane trimethacrylate, pentaerythritol, 1,3- and 1,4-cyclohexanediols, 1,3- and 1,4-cyclohexanedimethanols, hydrogenated bisphenol A, adducts of ethylene oxide and bisphenol A and adducts of propylene oxide and bisphenol A; epoxy compounds of glycidyl esters which are produced by condensation of epihalohydrins with polybasic carboxylic acid compounds such as adipic acid, sebacic acid, dodecandicarboxylic acid, dimer acid, phthalic acid, isophthalic acid, terephthalic acid, tetrahydrophthalic acid, methyltetrahydrophthalic acid, hexahydrophthalic acid, hexahydroisophthalic acid, hexahydroterephthalic acid, HET acid, nadic acid, maleic acid, succinic acid, fumaric acid, trimellitic acid, benzenetetracarboxylic acid, benzophenonetetracarboxylic acid, naphthalenedicarboxylic acid and diphenyldicarboxylic acid; epoxy compounds derived from amines which are produced by condensation of epihalohydrins with primary amines such as ethylenediamine, 1,2-diaminopropane, 1,3-diaminopropane, 1,2-diaminobutane, 1,3-diaminobutane, 1,4-diaminobutane, 1,5-diaminopentane, 1,6-diaminohexane, 1,7-diaminoheptane, 1,8-diaminooctane, bis(3-aminopropyl) ether, 1,2-bis(3-aminopropoxy)ethane, 1,3-bis(3-aminopropoxy)-2,2'-dimethylpropane, 1,2-, 1,3- and 1,4-bisaminocyclohexanes, 1,3- and 1,4-bisaminomethylcyclohexanes, 1,3- and 1,4-bisaminoethylcyclohexanes, 1,3- and 1,4-bisaminopropylcyclohexanes, hydrogenated 4,4'-diaminodiphenylmethane, isophoronediamine, 1,4-bisaminopropylpiperadine, m- and p-phenylenediamines, 2,4- and 2,6-tolylenediamines, m- and p-xylylenediamines, 1,5- and 2,6-naphthalenediamines, 4,4'-diaminodiphenylmethane, 4,4'-diaminodiphenyl ether, 2,2-(4,4'-diaminodiphenyl)propane, and secondary amines such as N,N'-dimethylethylenediamine, N,N'-dimethyl-1,2-diaminopropane, N,N'-dimethyl-1,3-diaminopropane, N,N'-dimethyl-1,2-diaminobutane, N,N'-dimethyl-1,3-diaminobutane, N,N'-dimethyl-1,4-diaminobutane, N,N'-dimethyl-1,5-diaminopentane, N,N'-dimethyl-1,6-diaminohexane, N,N'-dimethyl-1,7-diaminoheptane, N,N'-diemethylethylenediamine, N,N'-diethyl-1,2- diaminopropane, N,N'-diethyl-1,3-diaminopropane, N,N'-diethyl-1,2-diaminobutane, N,N'-diethyl-1,3-diaminobutane, N,N'-diethyl-1,4-diaminobutane, N,N'-diethyl-1,6-diaminohexane, piperadine, 2-methylpiperadine, 2,5- and 2,6-dimethylpiperadines, homopiperadine, 1,1-di(4-piperadyl)methane, 1,2-di(4-piperidyl)ethane, 1,3-di(4-piperidyl)propane and 1,4-di(4-piperidyl)butane; alicyclic epoxy compounds such as 3,4-epoxycyclohexyl 3,4-epoxycyclohexanecarboxylate, vinylcyclohexane dioxide, 2-(3,4-epoxycyclohexyl)-5,5-spiro-3,4-epoxycyclohexane-metadioxane and bis(3,4-epoxycyclohexyl)adipate; epoxy compounds produced by epoxidation of unsaturated compounds such as cyclopentadiene epoxide, epoxidized soy bean oil, epoxidized polybutadiene and vinylcyclohexene epoxide; and epoxy compounds of urethane produced from the above polyhydric alcohols or phenols, diisocyanates and glycidol.

Examples of the episulfide compound include episulfide compounds obtained by converting a portion of the epoxy groups or the entire epoxy groups in the above epoxy compounds into the episulfide group and epithioalkylthio compounds having, in one molecule, one or more structures represented by the following formula (19):

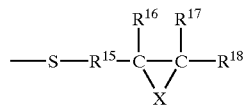

(19)

wherein $R^{15}$ represents a hydrocarbon group having 1 to 10 carbon atoms, $R^{16}$ to $R^{18}$ each represents hydrogen atom or a hydrocarbon group having 1 to 10 carbon atoms, X represents S or O and the average number of S represented by X is 50% or more of a total number of S and O constituting the three-membered ring. Preferable examples of the organic compound having one or more epithioalkylthio groups include compounds obtained by substituting one or more epoxyalkylthio groups such as β-epoxypropylthio group in an epoxy compound derived from a compound having a mercapto group and an epihalohydrin with an epithioalkylthio group. More specific examples include the following compounds.

Organic compounds having a chain aliphatic skeleton structure such as bis(β-epithiopropyl) sulfide, bis(β-epithiopropylthio)methane, 1,2-bis(β-epithiopropylthio)ethane, 1,3-bis(β-epithiopropylthio)propane, 1,2-bis(β-epithiopropylthio)propane, 1-(β-epithiopropylthio)-2-(β-epithiopropylthiomethyl)propane, 1,4-bis(β-epithiopropylthio)butane, 1,3-bis(β-epithiopropylthio)butane, 1-(β-epithiopropylthio)-3-(β-epithiopropylthiomethyl)butane, 1,5-bis(β-epithiopropylthio)pentane, 1-(β-epithiopropylthio)-4-(β-epithiopropylthiomethyl)pentane, 1,6-bis(β-epithiopropylthio)hexane, 1-(β-epithiopropylthio)-5-(β-epithiopropylthiomethyl)hexane, 1-(β-epithiopropylthio)-2-[(2-β-epithiopropylthioethyl)thio]ethane, 1-(β-epithiopropylthio)-2-[[2-(2-(β-epithiopropylthioethyl)thioethyl]thio]ethane, tetrakis(β-epithiopropylthiomethyl)methane, 1,1,1-tris(β-epithiopropylthiomethyl)propane, 1,5-bis(β-epithiopropylthio)-2-(-epithiopropylthiomethyl)-3-thiapentane, 1,5-bis(β-epithiopropylthio)-2,4-bis(β-epithiopropylthiomethyl)-3-thiapentane, 1-(β-epithiopropylthio)-2,2-bis(β-epithiopropylthiomethyl)-4-thiahexane, 1,5,6-tris(β-epithiopropylthio)-4-(β-epithiopropylthiomethyl)-3-thiahexane, 1,8-bis(β-epithiopropylthio)-4-(β-epithiopropylthiomethyl)-3,6-dithiaoctane, 1,8-bis(β-epithiopropylthio)-4,5-bis((3-epithiopropylthiomethyl)-3,6-dithiaoctane, 1,8-bis(β-epithiopropylthio)-4,4-bis(βepithiopropylthoimethyl)-3,6-dithiaoctane, 1,8-bis(β-epithiopropylthio)-2,4,5-tris(β-epithpopropylthiomethyl)-3,6-dithiaoctane, 1,8-bis(β-epithiopropylthio)-2,5-bis(β-epithiopropylthiomethyl)-3,6-dithiaoctane, 1,9-bis(β-epithiopropylthio)-5-(β-epithiopropylthiomethyl)-5-[(2-β-epithiopropylthioethyl)thiomethyl]-3,7-dithianonane, 1,10-bis(β-epithiopropylthio)-5,6-bis[(2-β-epithiopropylthioethyl)thio]-3,6,9-trithiadecane, 1,11-bis(β-epithiopropylthio)-4,8-bis(β-epithiopropylthiomethyl)-3,6,9-trithiaundecane, 1,11-bis(β-epithiopropylthio)-5,7-bis(β-epithiopropylthiomethyl)-3,6,9-trithiaundecane, 1,1 1-bis(β-epithiopropylthio)-5,7-[(2-β-epithiopropylthioethyl)thiomethyl]-3,6,9-trithiaundecane and 1,11-bis(β-epithiopropylthio)-4,7-bis(β-epithiopropylthiomethyl)-3,6,9-trithiaundecane.

Chain compounds having an ester group and an epithioalkylthio group such as tetra[2-(β-epithiopropylthio)acetylmethyl]methane, 1,1,1-tri[2-(β-epithiopropylthio)acetylmethyl]propane, tetra[2-(β-epithiopropylthiomethyl)acetylmethyl]methane and 1,1,1-tri[2-(β-epithiopropylthiomethyl)acetylmethyl]propane.

Compounds having an alicyclic skeleton structure such as 1,3- and 1,4-bis(β-epithiopropylthio)cyclohexanes, 1,3- and 1,4-bis(β-epithiopropylthiomethyl)cyclohexanes, bis [4-(β-epithiopropylthio)cyclohexyl]methane, 2,2-bis [4-(β-epithiopropylthio)cyclohexyl]propane, bis [4-(β-epithiopropylthio)cyclohexyl]sulfide, 2,5-bis(β-epithiopropylthiomethyl)-1,4-dithiane and 2,5-bis(β-epithiopropylthioethylthiomethyl)-1,4-dithiane.

Compounds having an aromatic skeleton structure such as 1,3- and 1,4-bis(β-epithiopropylthio)benzenes, 1,3- and 1,4-bis(β-epithiopropylthiomethyl)benzenes, bis [4-(β-epithiopropylthio)-phenyl]methane, 2,2-bis [4-(β-epithiopropylthio)phenyl]propane, bis[4-(β-epithiopropylthio)phenyl]sulfide, bis[4-(β-epithiopropylthio)phenyl]sulfone and 4,4'-bis(β-epithiopropylthio)biphenyl. The examples also include compounds obtained by substituting at least one hydrogen atom of the episulfide group in the above compounds with methyl group.

Specific examples of the compound having one functional group which are reactive with the episulfide group and/or the epoxy group and one or more other homopolymerizable functional groups are as follows.

Examples of the epoxy compound having unsaturated groups include vinylphenyl glycidyl ether, vinylbenzyl glycidyl ether, glycidyl methacrylate, glycidyl acrylate and allyl glycidyl ether. Examples of the episulfide compound having unsaturated groups include compounds obtained by substituting the epoxy group in the above epoxy compound having unsaturated group with the episulfide group, such as vinylphenyl thioglycidyl ether, vinylbenzyl thioglycidyl ether, thioglycidyl methacrylate, thioglycidyl acrylate and ally thioglycidyl ether.

Examples of the compound having one or more homopolymerizable functional groups include compounds having a structure of an ester of acrylic acid or methacrylic acid and a mono- or polyhydric alcohol such as methyl acrylate, methyl methacrylate, ethyl acrylate, ethyl methacrylate, ethylene glycol diacrylate, ethylene glycol dimethacrylate, diethylene glycol diacrylate, diethylene glycol dimethacrylate, triethylene glycol diacrylate, triethylene glycol dimethacrylate, polyethylene glycol diacrylate, polyethylene glycol dimethacrylate, 1,3-butylene glycol diacrylate, 1,3-butylene glycol dimethacrylate, 1,6-hexanediol diacrylate, 1,6-hexanediol dimethacrylate, neopentyl glycol diacrylate, neopentyl glycol dimethacrylate, polypropylene glycol diacrylate, polypropylene glycol dimethacrylate, 2,2-bis [4-(acryloxyethoxy)phenyl]propane, 2,2-bis [4-(methacryl oxyethoxy)phenyl]propane, 2,2-bis [4-(acryloxy•diethoxy)phenyl]propane, 2,2-bis [4-(methacryloxy•diethoxy)phenyl]propane, 2,2-bis[4-(acryloxy•polyethoxy)phenyl]propane, 2,2-bis[4-(methacryloxypolyethoxy)phenyl]propane, trimethylolpropane triacrylate, trimethylolpropane trimethacrylate, pentaerythritol tetraacrylate, pentaerythritol tetramethacrylate, bis(2,2,2-trimethylolethyl) ether hexaacrylate and bis(2,2,2-trimethylolethyl) ether hexamethacrylate; allyl compounds such as allyl sulfide, diallyl phthalate and diethylene glycol bisallyl carbonate; vinyl compounds such as acrolein, acrylonitrile and vinyl sulfide; and aromatic vinyl compounds such as styrene, α-methylstyrene, methylvinylbenzene, ethylvinylbenzene, α-chlorostyrene, chlorovinylbenzene, vinylbenzyl chloride, para-divinylbenzene and meta-divinylbenzene.

The above compounds having two or more functional groups which are reactive with tile episulfide group and/or the epoxy group and the above compounds having one or more such functional groups and one or more other homopolymerizable functional group can be cured by polymerization in the presence of a curing catalyst. As the curing catalyst, amines, phosphines and acids described above can be used. Examples of the curing catalyst are the same as the compounds described as the examples of the amines, phosphines and acids described above.

When the compound having unsaturated groups is used, it is preferable that a radical polymerization initiator is used as the polymerization accelerator. Any compound forming a radical by heating or by irradiation of ultraviolet light or electron beams can be used as the radical polymerization initiator. Examples of the radical polymerization initiator include the following conventional polymerization catalysts used under heating: peroxides such as cumyl peroxyneodecanoate, diisopropyl peroxydicarbonate, diallyl peroxydicarbonate, di-n-propyl peroxydicarbonate, dimyristyl peroxydicarbonate, cumyl peroxyneohexanoate, tert-hexyl peroxyneodecanoate, tert-butyl peroxyneodecanoate, tert-hexyl peroxyneohexanoate, tert-butyl peroxyneohexanoate, 2,4-dichlorobenzoyl peroxide, benzoyl peroxide, dicumyl peroxide and di-tert-butyl peroxide, hydroperoxides such as cumene hydroperoxide and tert-butyl hydroperoxide, and azo compounds such as 2,2'-azobis(4-methoxy-2,4-dimethylvaleronitrile), 2,2'-azobis(2-cyclopropylpropionitrile), 2,2'-azobis-(2,4-dimethylvaleronitrile), 2,2'-azobisisobutyronitrile, 2,2'-azobis(2-methylbutyronitrile), 1,1'-azobis(cyclohexane-1-carbonitrile), 1-[(1-cyano-1-methylethyl)azo]formamide, 2-phenylazo-4-methoxy-2,4-dimethylvaleronitrile, 2,2'-azobis(2-methylpropane) and 2,2'-azobis(2,4,4-trimethylpentane); and conventional photopolymerization catalysts such as benzophenone and benzoin benzoinmethyl ether. Among these compounds, peroxides, hydroperoxides and azo compounds are preferable and peroxides and azo compounds are more preferable. Most preferable examples include azo compounds such as 2,2'-azobis(4-methoxy-2,4-dimethylvaleronitrile), 2,2'-azobis(2-cyclopropylpropionitrile), 2,2'-azobis-(2,4-dimethylvaleronitrile), 2,2'-azobisisobutyronitrile, 2,2'-azobis(2-methylbutyronitrile), 1,1'-azobis(cyclohexane-1-carbonitrile), 1-[(1-cyano-1-methylethyl)azo]formamide, 2-phenylazo-4-methoxy-2,4-dimethylvaleronitrile, 2,2'-azobis(2-methylpropane) and 2,2'-azobis(2,4,4-trimethylpentane. The above compounds may be used as a mixture of the compounds.

The amount of the radical polymerization initiator is different depending on the components of the composition and the process for curing. The amount is generally in the range of 0.01 to 5.0% by weight and preferably in the range of 0.1 to 2.0% by weight of the total amount of the composition.

When optical materials are obtained by curing a composition containing the ether compound of the present invention by polymerization, it is, of course, possible that conventional additives such as antioxidants and ultraviolet light absorbents are added to improve the practical properties of the obtained materials. The composition tends to be cleaved from molds during polymerization. Therefore, it is occasionally necessary that conventional external and/or internal adhesion improvers are used or added to control and improve adhesion between the cured material obtained and the mold. Examples of the internal adhesion improver include silane compounds such as 3-methacryloxypropyltrimethoxysilane, 3-glycidoxypropyltrimethoxysilane, N-(2-aminoethyl)-3-aminopropyltrimethoxysilane and 3-mercaptopropyltrimethoxysilane. The internal adhesion improver call be used in an amount of 0.0001 to 5 parts by weight per 100 parts by weight of the ether compound of the present invention. It is also possible that the property to release the obtained cured material from the molds is improved by using or adding a conventional external and/or internal mold release. Examples of the internal mold release include nonionic surfactants containing fluorine, nonionic surfactants containing silicon, quaternary alkylammonium salts, esters of phosphoric acid, esters of hydrogenphosphoric acid, esters of phosphoric acid of oxyalkylene types, alkali metal salts of esters of hydrogenphosphoric acid, alkali metal salts of hydrogenphosphoric acid of oxyalkylene types, metal salts of higher fatty acids, esters of higher fatty acids, paraffin, wax, higher aliphatic amides, higher aliphatic alcohols, polysiloxanes and addition products of ethylene oxide to aliphatic amines.

To obtain the novel optical material of the cured resin of the present invention in accordance with curing by polymerization, the diepisulfide ether compound of the present invention, the compound having one or more SH groups used as the antioxidation component, the compound having one or more active hydrogen atoms in one molecule, at least one of the active hydrogen atoms being other than that of the SH group, which is used to improve the tint performance and other additives such as adhesion improvers, mold releases, conventional antioxidants and ultraviolet absorbents are mixed together and the prepared mixture is cured by polymerization to produce optical materials such as lenses. The mixture is cast into a mold made of glass or metal and cured by heating and the cured product is then taken out of the mold.

The curing time is 0.1 to 100 hours and generally 1 to 48 hours. The curing temperature is −10 to 160° C. and generally −10 to 140° C. To remove residual strains from the optical material of the present invention, it is preferable that the material obtained after the curing is annealed at a temperature of 50 to 150° C. for about 10 minutes to 5 hours. Where necessary, the prepared material may have surface treatments such as formation of hard coat, a treatment for prevention of reflection and a treatment for prevention of clouding.

The process for producing the optical material of the cured resin of the present invention is described more specifically in the following. The main materials and the auxiliary materials are mixed together as described above and the obtained mixture is cast into a mold and cured. The diepisulfide ether compound as the main material and components which are optionally used may be mixed together in one vessel at the same time in the entire amounts. Alternatively, the components may be added stepwise. Some components may also be mixed together separately in advance and the obtained mixtures may be mixed together in one vessel. The main materials and the auxiliary materials may be mixed together in any desired order. In general, the temperature of mixing and the time of mixing are not limited as long as the components can be sufficiently mixed together. However, an excessively high temperature and an excessively long time are not preferable because undesirable reactions takes place between the components and viscosity increases to cause difficulty in the operation of casting.

The temperature of mixing should be in the range of about −100 to 100° C., preferably in the range of −50 to 50° C. and more preferably in the range of −5 to 30° C. The time of mixing is in the range of 1 minute to 5 hours, preferably in the range of 5 minutes to 2 hours, more preferably in the range of 5 to 30 minutes and most preferably in the range of about 5 to 15 minutes. It is preferable that degassing is conducted at a reduced pressure before, during or after mixing the materials and the additives to prevent formation of bubbles during casting and curing in the mold. The pressure of the degassing is 0.1 to 700 mmHg and preferably 10 to 300 mmHg. To obtain a better quality of the optical material of the present invention, it is preferable that impurities are removed by filtration using a microfilter having a pore diameter of about 0.1 to 5 μm or the like before the casting.

To summarize the advantages of the present invention, when the optical material of the cured resin obtained by curing the ether compound of the present invention by polymerization is used, an excellent balance between a sufficiently large refractive index and a sufficiently large Abbe number, excellent tint performance and an excellent antioxidation property can be achieved. As long as conventional compounds are used as the material, it is difficult that these properties are achieved.

EXAMPLES

The present invention is described more specifically with reference to the following examples. However, the present invention is not limited to the examples. The physical properties of the obtained polymers were evaluated using plate-shaped test pieces having a thickness of 2 mm in accordance with the following methods.

Refractivity index (nD) and Abbe number (vD): The refractivity index and the Abbe number were measured at 25° C. using an Abbe refractometer.

Tint performance: A sample was dipped into an aqueous tinting bath having the following composition at a temperature of 95° C. for 30 minutes:

| SEIKO PRAX DIACOAT BROWN D | 0.2% by weight |
| SEIKO PRAX tinting auxiliary agent | 0.3% by weight |
| benzyl alcohol | 2.0% by weight |

The tint performance was obtained in accordance with the following equation:

Tint performance=100−total light transmittance after tinting (%)

Color tone: The b-value was measured using a spectrometric calorimeter. The smaller the b-value, the thinner the yellow color.

Antioxidation property: The antioxidation property was evaluated by the measurement of the increase in the b-value after a test piece had been heated at 120° C. for 3 hours in the atmosphere of the air.

Example 1

Into a flask equipped with a stirrer, a dropping funnel, a thermometer and an inlet for nitrogen, 390 g of bis(β-epoxypropyl) ether, 1 kg of thiourea, 2.5 liters of toluene as a solvent and 2.5 liters of methanol also as a solvent were placed and the reaction was allowed to proceed at 30° C. for 9 hours. After the reaction was completed, the insoluble fraction was removed by filtration. The filtrate was extracted with toluene and the extract was washed with a 1% aqueous solution of sulfuric acid and then with water. After the excess amounts of the solvents were removed by distillation, a colorless transparent oil was obtained. As the results of the elemental analysis, the mass analysis and the IR analysis, the obtained oil was found to be bis(β-epithiopropyl) ether. The result of the elemental analysis is shown below. The mass spectrum showed a value of $M^+$ of 162 (the theoretical molecular weight: 162). In the IR analysis, the absorption assigned to stretching vibration of the ether bond was found at 1100 $cm^{-1}$ and the absorption assigned to stretching vibration of the episulfide ring was found at 620 $cm^{-1}$.

|  | H | S | C |
| --- | --- | --- | --- |
| Found (%) | 44.21 | 6.45 | 39.40 |
| Calculated (%) | 44.41 | 6.21 | 39.52 |

Example 2

Into a flask equipped with a stirrer, a dropping funnel, a thermometer and an inlet for nitrogen, 475 g of bis(β-methyl-β-epoxypropyl) ether, 1 kg of thiourea, 2.5 liters of toluene as a solvent and 2.5 liters of methanol also as a solvent were placed and the reaction was allowed to proceed at 30° C. for 9 hours. After the reaction was completed, the insoluble fraction was removed by filtration. The filtrate was extracted with toluene and the extract was washed with a 1% aqueous solution of sulfuric acid and then with water. After the excess amounts of the solvents were removed by distillation, a colorless transparent oil was obtained. As the results of the elemental analysis, the mass analysis and the IR analysis, the obtained oil was found to be bis(β-methyl-β-epithiopropyl) ether. The result of the elemental analysis is shown below. The mass spectrum showed a value of $M^+$ of 190 (the theoretical molecular weight: 190). In the IR analysis, the absorption assigned to stretching vibration of the ether bond was found at 1100 $cm^{-1}$ and the absorption assigned to stretching vibration of the episulfide ring was found at 620 $cm^{-1}$.

|  | H | S | C |
|---|---|---|---|
| Found (%) | 50.31 | 7.58 | 33.54 |
| Calculated (%) | 50.48 | 7.41 | 33.70 |

Example 3

Into a flask equipped with a stirrer, a dropping funnel, a thermometer and an inlet for nitrogen, 433 g of (β-epoxypropyl) (β-methyl-β-epoxypropyl) ether, 1 kg of thiourea, 2.5 liters of toluene as a solvent and 2.5 liters of methanol also as a solvent were placed and the reaction was allowed to proceed at 30° C. for 9 hours. After the reaction was completed, the insoluble fraction was removed by filtration. The filtrate was extracted with toluene and the extract was washed with a 1% aqueous solution of sulfuric acid and then with water. After the excess amounts of the solvents were removed by distillation, a colorless transparent oil was obtained. As the results of the elemental analysis, the mass analysis and the IR analysis, the obtained oil was found to be (β-epithiopropyl) (β-methyl-β-epithiopropyl) ether. The result of the elemental analysis is shown below. The mass spectrum showed a value of $M^+$ of 176 (the theoretical molecular weight: 176). In the IR analysis, the absorption assigned to stretching vi)ration of the ether bond was found at 1100 cm$^{-1}$ and the absorption assigned to stretching vibration of the episulfide ring was found at 620 cm$^{-1}$.

|  | H | S | C |
|---|---|---|---|
| Found (%) | 47.51 | 7.00 | 36.25 |
| Calculated (%) | 47.69 | 6.86 | 36.38 |

Example 4

Into a flask equipped with a stirrer, a dropping funnel, a thermometer and an inlet for nitrogen, 571 g of (β-epoxypropyl) (β-epoxypropylthioethyl) ether, 1 kg of thiourea, 2.5 liters of toluene as a solvent and 2.5 liters of methanol also as a solvent were placed and the reaction was allowed to proceed at 30° C. for 9 hours. After the reaction was completed, the insoluble fraction was removed by filtration. The filtrate was extracted with toluene and the extract was washed with a 1% aqueous solution of sulfuric acid and then with water. After the excess amounts of the solvents were removed by distillation, a colorless transparent oil was obtained. As the results of the elemental analysis, the mass analysis and the IR analysis, the obtained oil was found to be (β-epithiopropyl) (β-epithiopropylthioethyl) ether. The result of the elemental analysis is shown below. The mass spectrum showed a value of $M^+$ of 222 (the theoretical molecular weight: 222). In the IR analysis, the absorption assigned to stretching vibration of the ether bond was found at 1100 cm$^{-1}$ and the absorption assigned to stretching vibration of the episulfide ring was found at 620 cm$^{-1}$.

|  | H | S | C |
|---|---|---|---|
| Found (%) | 43.00 | 6.48 | 43.11 |
| Calculated (%) | 43.21 | 6.21 | 43.26 |

Example 5

To 100 parts by weight of bis(β-epithiopropyl) (β-epithiopropylthioethyl) ether, 0.2 parts by weight of N,N-diethanolamine was added as the catalyst and a homogeneous solution of the mixture was prepared. After the obtained solution was sufficiently degassed at a reduced pressure of 10 mm Hg, the solution was cast into a mold and cured by polymerization under heating in an oven while the temperature was raised from 40° C. to 100° C. over 10 hours. The physical properties of a plate-shaped test piece of the obtained material are shown in Table 1. The refractive index and the Abbe number both showed high values which cannot be obtained in accordance with conventional technology. The tint performance was sufficiently excellent. The test piece exhibited excellent transparency without marked yellow color.

Example 6 bis(β-Epithiopropyl) ether in an amount of 100 parts by weight was sufficiently degassed at a reduced pressure of 10 mm Hg. To the degassed compound, 1 part by weight of piperidine was added as the catalyst and a homogeneous solution of the mixture was prepared. Then, the solution was cast into a mold and cured by polymerization under heating in an oven while the temperature was raised from 40° C. to 100° C. over 10 hours. The physical properties of a plate-shaped test piece of the obtained material are shown in Table 1. The refractive index and the Abbe number both showed high values which cannot be obtained in accordance with conventional technology. The tint performance was sufficiently excellent. The test piece exhibited excellent transparency without marked yellow color.

Example 7 bis(β-Epithiopropyl) ether in an amount of 100 parts by weight was sufficiently degassed at a reduced pressure of 10 mm Hg. To this compound, 0.2 parts by weight of triethylamine was added as the catalyst and a homogeneous solution of the mixture was prepared. Then, the solution was cast into a mold and cured by polymerization under heating in an oven while the temperature was raised from 40° C. to 100° C. over 10 hours. The physical properties of a plate-shaped test piece of the obtained material are shown in Table 1.

Example 8

To 100 parts by weight of bis(β-epithiopropyl) ether, 0.58 parts by weight of N,N-diethylethanolamine was added as the catalyst and a homogeneous solution of the mixture was prepared. After the solution was degassed at a reduced pressure of 10 mm Hg, the solution was cast into a mold and cured by polymerization under heating in an oven while the temperature was raised from 40° C. to 100° C. over 10 hours. The physical properties of a plate-shaped test piece of the obtained material are shown in Table 1.

Example 9

To 100 parts by weight of bis(β-methyl-β-epithiopropyl) ether, 0.58 parts by weight of N,N-diethylethanolamine was added as the catalyst and a homogeneous solution of the mixture was prepared. After the solution was degassed at a reduced pressure of 10 mm Hg, the solution was cast into a mold and cured by polymerization under heating in an oven while the temperature was raised from 40° C. to 100° C. over 10 hours. The physical properties of a plate-shaped test piece of the obtained material are shown in Table 1.

Example 10

To 100 parts by weight of (β-epithiopropyl) (β-methyl-β-epithiopropyl) ether, 0.58 parts by weight of N,N-diethylethanolamine was added as the catalyst and a homogeneous solution of the mixture was prepared. After the solution was degassed at a reduced pressure of 10 mm Hg, the solution was cast into a mold and cured by polymerization under heating in an oven while the temperature was raised from 40° C. to 100° C. over 10 hours. The physical properties of a plate-shaped test piece of the obtained material are shown in Table 1.

Comparative Example 1 bis(β-Epithiopropyl) sulfide in an amount of 100 parts by weight was sufficiently degassed at a reduced pressure of 10 mm Hg. Then, 0.2 parts by weight of triethylamine was added as the catalyst and a homogeneous solution of the mixture was prepared. Then, the solution was cast into a mold and cured by polymerization under heating in an oven while the temperature was raised from 40° C. to 100° C. over 10 hours. The physical properties of a plate-shaped test piece of the obtained material are shown in Table 1. Tint performance was poor because of the absence of the ether bond.

Comparative Example 2 bis(β-Methyl-β-epithiopropyl) sulfide in an amount of 100 parts by weight was sufficiently degassed at a reduced pressure of 10 mm Hg. Then, 0.2 parts by weight of triethylamine was added as the catalyst and a homogeneous solution of the mixture was prepared. Then, the solution was cast into a mold and cured by polymerization under heating in an oven while the temperature was raised from 40° C. to 100° C. over 10 hours. The physical properties of a plate-shaped test piece of the obtained material are shown in Table 1. Tint performance was poor because of the absence of the ether bond.

Comparative Example 3

To a mixture of 48 parts by weight of 1,8-dimercapto-4-mercaptomethyl-3,6-dithiaoctane and 52 parts by weight of meta-xylylene diisocyanate, dibutyltin chloride was added as the catalyst in an amount of 0.1 part by weight per 100 parts by weight of the mixture. After a homogeneous solution of the mixture was prepared, the solution was sufficiently degassed at a reduced pressure of 10 mmHg. The solution was then cast into a mold and cured by polymerization in an oven at 80° C. for 20 hours. The physical properties of a plate-shaped test piece of the obtained material are shown in Table 1. The refractive index and the Abbe number did not show a satisfactory balance.

TABLE 1

| | Compound | nD | vD | tint performance | color tone | antioxidation property |
|---|---|---|---|---|---|---|
| Example 5 | bis(β-epithiopropyl) (β-epithiopropyl-thioethyl) ether | 1.67 | 39 | 60% | 0.35 | 0.10 |
| Example 6 | bis(β-epithiopropyl) ether | 1.65 | 41 | 55% | 0.35 | 0.10 |
| Example 7 | bis(β-epithiopropyl) ether | 1.65 | 41 | 55% | 0.30 | 0.10 |
| Example 8 | bis(β-epithiopropyl) ether | 1.65 | 41 | 55% | 0.30 | 0.10 |
| Example 9 | bis(β-methyl-β-epithiopropyl) ether | 1.63 | 43 | 55% | 0.35 | 0.05 |
| Example 10 | (β-epithiopropyl) (β-methyl-β-epithiopropyl) ether | 1.64 | 42 | 50% | 0.30 | 0.10 |
| Comparative Example 1 | bis(β-epithiopropyl) sulfide | 1.71 | 36 | 25% | 0.35 | 0.25 |
| Comparative Example 2 | bis(β-methyl-β-epithiopropyl) sulfide | 1.67 | 39 | 25% | 0.40 | 0.20 |
| Comparative Example 3 | 1,8-dimercapto-4-mercaptomethyl-3,6-dithiaoctane/m-xylylene diisocyanate = 48/52 | 1.66 | 32 | 85% | 0.40 | 0.15 |

What is claimed is:

1. A process for producing a lens comprising polymerizing bis(β-epithiopropyl)ether to form a lens.

2. The process of claim 1, wherein the polymerizing includes casting the bis(β-epithiopropyl)ether into a mold and carrying out curing.

3. The process of claim 2, wherein the curing is carried out for 0.1 to 100 hours.

4. The process of claim 2, wherein the curing is carried out for 1 to 48 hours.

5. The process of claim 4, wherein the curing is carried out at a temperature of −10 to 160° C.

6. The process of claim 4, wherein the curing is carried out at a temperature of −10 to 140° C.

7. The process of claim 1, wherein the polymerization is carried out in the presence of a curing catalyst selected from the group consisting of an amine, a phosphine, a mineral acid, a Lewis acid, an organic acid, a silicic acid and tetrafluoroboric acid.

8. The process of claim 7, wherein the curing catalyst is in an amount of 0.0001 to 1 mol per 1 mol of the bis (β-epithiopropyl) ether.

9. The process of claim 7, wherein the curing catalyst is in an amount of 0.0001 to 0.5 mol per 1 mol of the bis (β-epithiopropyl) ether.

10. The process of claim 7, wherein the curing catalyst is in an amount of 0.0001 to 0.05 mol per 1 mol of the bis (βepithiopropyl) ether.

* * * * *